(12) United States Patent
Woolley et al.

(10) Patent No.: US 9,079,670 B2
(45) Date of Patent: Jul. 14, 2015

(54) AEROSOL DETECTION

(75) Inventors: Alan Michael Woolley, Bedford Befordshire (GB); Stephen David Mobbs, Harrogate (GB); James Matthew Haywood, Woodbury (GB)

(73) Assignees: UNIVERSITY OF LEADS, Leads (GB); SECRETARY OF STATE FOR BUSINESS, INNOVATION AND SKILLS OF THE UNITED KINGDOM OF GREAT BRITAIN AND NORTHERN IRELAND, London (GB); NATURAL ENVIRONMENT RESEARCH COUNCIL, Swindon (GB)

( * ) Notice: Subject to any disclaimer, the term of this patent is extended or adjusted under 35 U.S.C. 154(b) by 266 days.

(21) Appl. No.: 13/821,873

(22) PCT Filed: Sep. 19, 2011

(86) PCT No.: PCT/GB2011/051757
§ 371 (c)(1),
(2), (4) Date: Mar. 25, 2013

(87) PCT Pub. No.: WO2012/042242
PCT Pub. Date: Apr. 5, 2012

(65) Prior Publication Data
US 2013/0193978 A1 Aug. 1, 2013

(30) Foreign Application Priority Data
Sep. 27, 2010 (GB) .................................. 1016222.0

(51) Int. Cl.
*G01R 29/12* (2006.01)
*B64D 45/00* (2006.01)
(Continued)

(52) U.S. Cl.
CPC ............ *B64D 45/00* (2013.01); *G01N 15/0637* (2013.01); *G01N 15/0656* (2013.01); *G01R 29/12* (2013.01); *G01W 1/08* (2013.01)

(58) Field of Classification Search
CPC ................................. G01W 1/08; G01R 29/12
USPC ................ 324/657–658, 71.3–71.4, 457, 109
See application file for complete search history.

(56) References Cited

U.S. PATENT DOCUMENTS 3,525,866 A * 8/1970 Sagalyn et al. ............ 250/336.1
3,820,026 A * 6/1974 Messinger .................... 340/945
(Continued)

FOREIGN PATENT DOCUMENTS

GB    1 382 226    1/1995

OTHER PUBLICATIONS

Hucke, "Preiptation-Static Interference on Aircraft and at Ground stations", Proceedings of the I.R.E., May 1939, p. 301-316.*
(Continued)

*Primary Examiner* — Patrick Assouad
*Assistant Examiner* — Lamarr Brown
(74) *Attorney, Agent, or Firm* — Foley & Lardner LLP (57) ABSTRACT

Aerosol detection apparatus comprises an aircraft having a dielectric member, such as a window (10), comprised in the body (12) thereof such that a surface of the dielectric member forms part of the exterior surface of the aircraft. Detection means (16), such as a static monitor is located on the inside of the aircraft and arranged to detect an electric field resulting from polarization of the dielectric member. The output of the static monitor, or the rate of change thereof, correlates closely to particle density as the aircraft is flown though an aerosol, such as a volcanic ash cloud. The apparatus is simple and relatively inexpensive, and may comprise any general purpose aircraft. Aerosol particles may be detected and mapped using apparatus of the invention more easily and quickly than by use of devices such as optical spectrometers mounted on dedicated research aircraft, or static monitors mounted on the exterior of an aircraft.

15 Claims, 6 Drawing Sheets

(51) Int. Cl.
  *G01N 15/06* (2006.01)
  *G01W 1/08* (2006.01)

(56) References Cited

U.S. PATENT DOCUMENTS

| | | | | |
|---|---|---|---|---|
| 3,846,700 | A * | 11/1974 | Sasaki et al. | 324/72 |
| 3,906,308 | A * | 9/1975 | Amason et al. | 361/218 |
| 4,005,357 | A * | 1/1977 | Parkinson | 324/457 |
| 4,101,825 | A * | 7/1978 | Truax | 324/458 |
| 4,262,254 | A * | 4/1981 | Poss | 324/457 |
| 4,277,771 | A * | 7/1981 | Chapin et al. | 340/979 |
| 4,328,461 | A * | 5/1982 | Butters et al. | 324/72 |
| 4,931,740 | A * | 6/1990 | Hassanzadeh et al. | 324/457 |
| 5,443,912 | A * | 8/1995 | Olson | 428/425.6 |
| 5,654,700 | A | 8/1997 | Brata et al. | |
| 6,900,642 | B2 * | 5/2005 | Zank et al. | 324/457 |
| 7,894,134 | B1 * | 2/2011 | Hauser | 359/490.02 |
| 8,410,784 | B1 * | 4/2013 | Brown et al. | 324/457 |
| 8,723,694 | B1 * | 5/2014 | Finley et al. | 340/970 |
| 2003/0021076 | A1 * | 1/2003 | Sillence et al. | 361/218 |
| 2005/0275415 | A1 * | 12/2005 | Sato et al. | 324/662 |
| 2006/0028447 | A1 * | 2/2006 | Vook | 345/163 |
| 2008/0246490 | A1 | 10/2008 | Brown et al. | |
| 2009/0014693 | A1 * | 1/2009 | Zahn | 252/510 |
| 2010/0259272 | A1 * | 10/2010 | Care | 324/457 |

OTHER PUBLICATIONS

Frederickson, "Electric Discharge Pulses in Irradiated Solid Dielectrics in Space", IEEE Transactions on Electrical Insulation, vol. EI-18, No. 3, Jun. 1983, p. 337-349.*

Edwards et al., "Meteorological Aspects of Precipitation Static", Journal of Meteorology, vol. 2, No. 4, Dec. 1945, p. 205-213.*

Waddel et al., "Part II—Aircraft Instrumentation for Precipitation-Static Research", Proceedings of the I.R.E. and Waves and Electrons, Apr. 1946, p. 161-166.*

International Preliminary Report on Patentability for PCT/GB2011/051757, issued Nov. 22, 2012.

International Search Report for PCT/GB2011/051757, issued Feb. 1, 2012.

Search Report for GB1016222.0 issued Dec. 16, 2010, one page.

* cited by examiner

AEROSOL DETECTION

CROSS-REFERENCE TO RELATED APPLICATIONS

The present application is a U.S. national stage application claiming the benefit of International Application No. PCT/GB2011/051757, filed on Sep. 19, 2011, which claims priority from Great Britain Patent Application No. 1016222.0, filed Sep. 27, 2010, the entire contents of which are incorporated herein by reference in their entirety.

The invention relates to apparatus and methods for aerosol detection, and particularly to the detection of solid particles, such as particles of ash, dust, ice, snow, rain or pollution, in the atmosphere.

Airborne particulates are typically detected and analysed over large regions of the atmosphere by means of complex particle-sensing instrumentation mounted on aircraft. For example, an aerosol spectrometer may be mounted on an aircraft, and the aircraft may then be flown through the atmosphere with air being drawn through the spectrometer by a vacuum pump. Certain commercially available aerosol spectrometers, such as the Model 1.129 Sky-OPC manufactured by Grimm Aerosol Technik GmbH & Co KG, are specifically designed for atmospheric research, and allow data relating to particle size and particle density to be recorded on an integrated data storage card as a function of time and/or the position of an aircraft on which the spectrometer is mounted. However such devices are complex and expensive. They require significant time and effort to be fitted to aircraft. Particle analysis in such devices is typically carried out by means of optical scattering measurements in which light from a laser or LED is scattered by the particles, and the presence, size and density of the particles is inferred from measurements of scattered light. This involves a complex arrangement of detectors and complex computer processing resources. Furthermore, dedicated research aircraft are generally required because of aircraft safety certification regulations. This means that commercial aircraft which fly through a given region of the atmosphere, and which could potentially gather data on airborne particulates as a function of position in the region, are not able to be exploited to gather such data.

A first aspect of the present invention provides aerosol detection apparatus comprising an aircraft having a dielectric member comprised in the body thereof such that a surface of the dielectric member forms part of the exterior surface of the aircraft, and detection means located in the interior of the aircraft and arranged to detect an electric field resulting from polarisation of the dielectric member.

When the aircraft is flown through airspace containing airborne particles, such as dust or ash for example, the dielectric member becomes polarised so that induced charge appears on the surface of the dielectric member opposite to that forming part of the exterior surface of the aircraft. By detecting an electric field within the aircraft resulting from this induced charge, the presence of particles in the atmosphere may be inferred. Since the bodies of aircraft are typically metallic, it has previously been assumed that if an aircraft were to become charged for any reason, no electric field would be present in the interior of the aircraft because the aircraft would behave as a Faraday cage. For example, aircraft charging has been noted previously, but detected by placing instruments on the exterior of an aircraft (R. C. Roberts & G. W. Brock, Journal of Meteorology, volume 2 (1945), pp 205-213; R. C. Waddel, R. C. Drutowski & W. N. Blatt, Proceedings of the Institute of Radio Engineers, volume 34 (1946), pp 161-166). The polarisation of the dielectric member may take place by one or more of a number of different mechanisms. Aerosol particles which are already charged can transfer their charge to the surface of the dielectric member forming part of the exterior of the aircraft, as the aircraft is flown through the aerosol. Uncharged aerosol particles may also cause charging of that surface by a frictional mechanism. Also, other parts of the exterior surface of the aircraft may become charged during flight through an aerosol, producing an electric field which polarises the dielectric member, or assists in the polarisation of the dielectric member.

The dielectric member may be a window of the aircraft, in which case any general purpose aircraft may be used. In other words no special dielectric member is required to be retro-fitted to an aircraft, or used in the construction of a new aircraft, in order to implement the invention. For example, a window of BAe '146' aircraft comprises an external layer of acrylic, which serves well as a dielectric member.

The detection means may be a static monitor mounted within the aircraft. An electro-static voltmeter, such as electro-mechanical field mill instrument, may be used. A suitable electro-mechanical field mill is the JCI 140 static monitor manufactured by Chilworth Technology Ltd of Southampton, U.K.

The apparatus may further comprise alarm means arranged to monitor an output of the static monitor and generate and alarm if said output exceeds a pre-determined threshold. The alarm could be a visual and/or audible signal for the attention of one or members of the aircrew. Additionally or alternatively it may be a control signal to the aircraft control systems causing the aircraft to move out of a certain region of airspace.

Preferably the apparatus further comprises a data acquisition system arranged to record the output of the static monitor, or the rate of change of the output of the static monitor, as a function of position of the aircraft. The electric field resulting from accumulated charge on the surface of the dielectric as the aircraft is flown through airspace containing particles indicates the presence of an aerosol. Recording the output of the static monitor (or its rate of change) as a function of position allows the presence of aerosol particles to be mapped.

Aircraft position may be obtained in a number of ways. For example when flying at constant velocity, total elapsed flight time is a measure of aircraft position. However in order to give accurate and detailed positional information (latitude, longitude and altitude), and hence more accurate and detailed mapping of the presence of particles in the atmosphere, the apparatus preferably further includes a global positioning system (GPS) arranged to output positional information for the aircraft to the data acquisition system.

The value of the electric field resulting polarisation of the dielectric member (and hence the output of the static monitor) may be a function of aerosol particle density. The rate of change of the electric field (and hence the rate of change of the output of the static monitor) may also be a function of aerosol particle density. The apparatus therefore preferably further includes processing means arranged to convert recorded values of the output of the static monitor, or as the case may be recorded values of the rate of change of the output of the static monitor, to values of aerosol particle density on the basis of an assumed functional form for aerosol particle density as a function of the output, or as the case may be the rate of change of the output, of the static monitor. This allows aerosol particle density to be mapped, i.e. aerosol particle density to be determined as a function of aircraft position. The assumed functional form may be linear or non-linear depending on the circumstances, for example the type of particle in the atmosphere.

Figure 1:
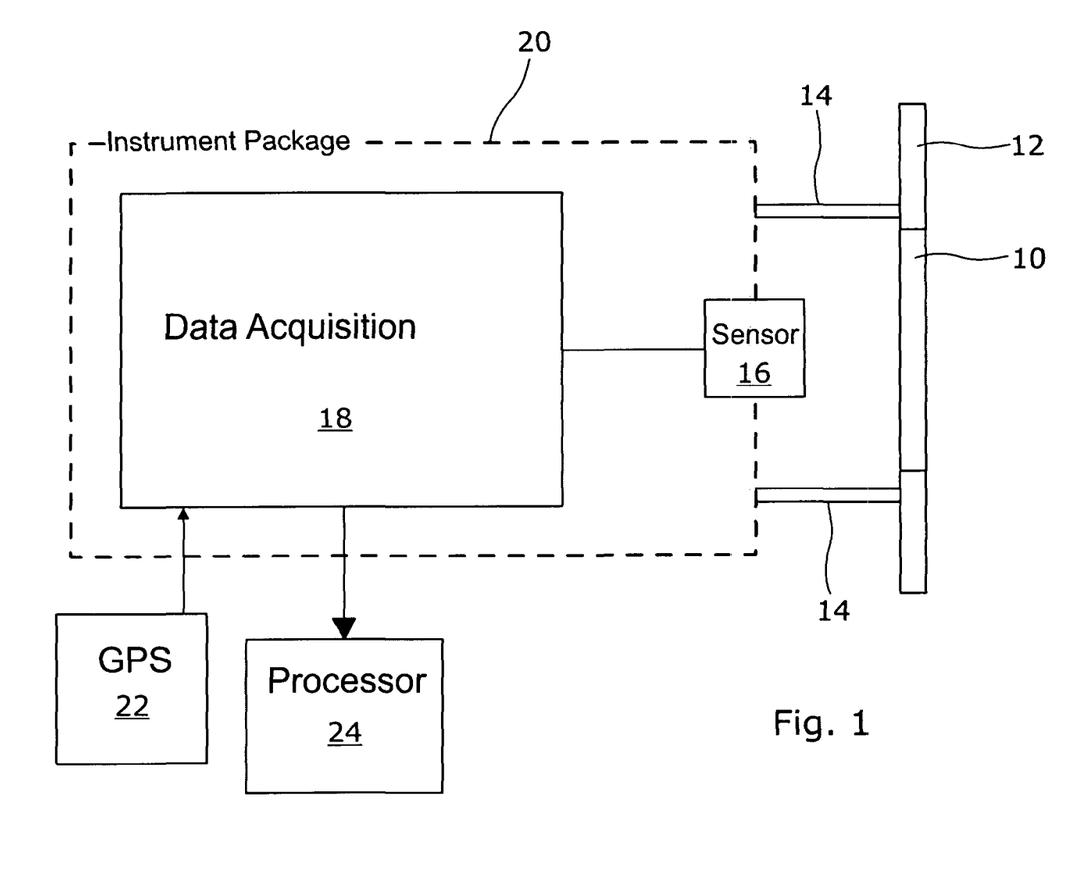
Figure 2:
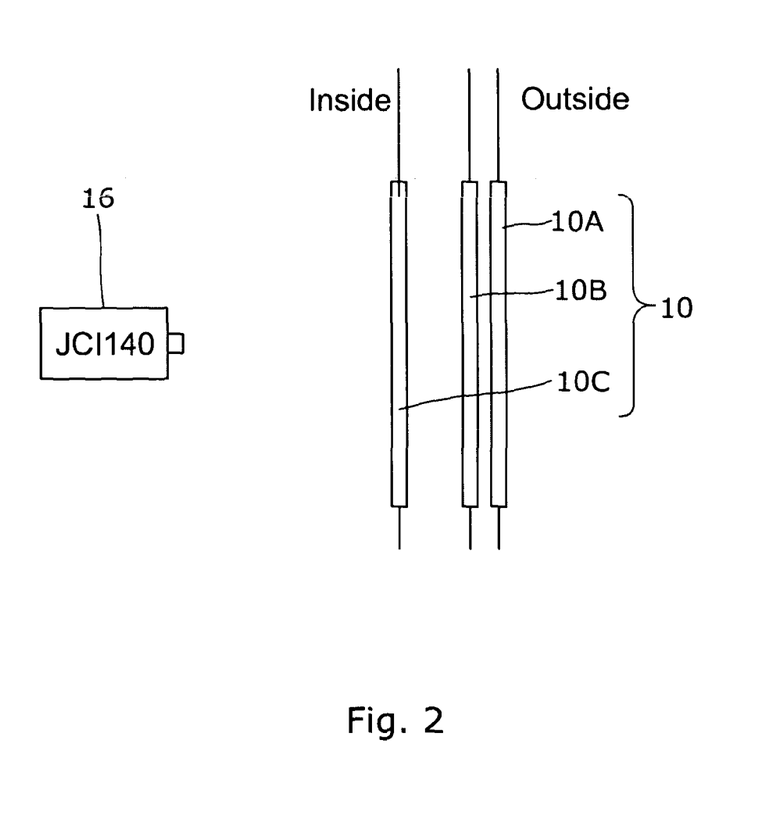
Figure 3:
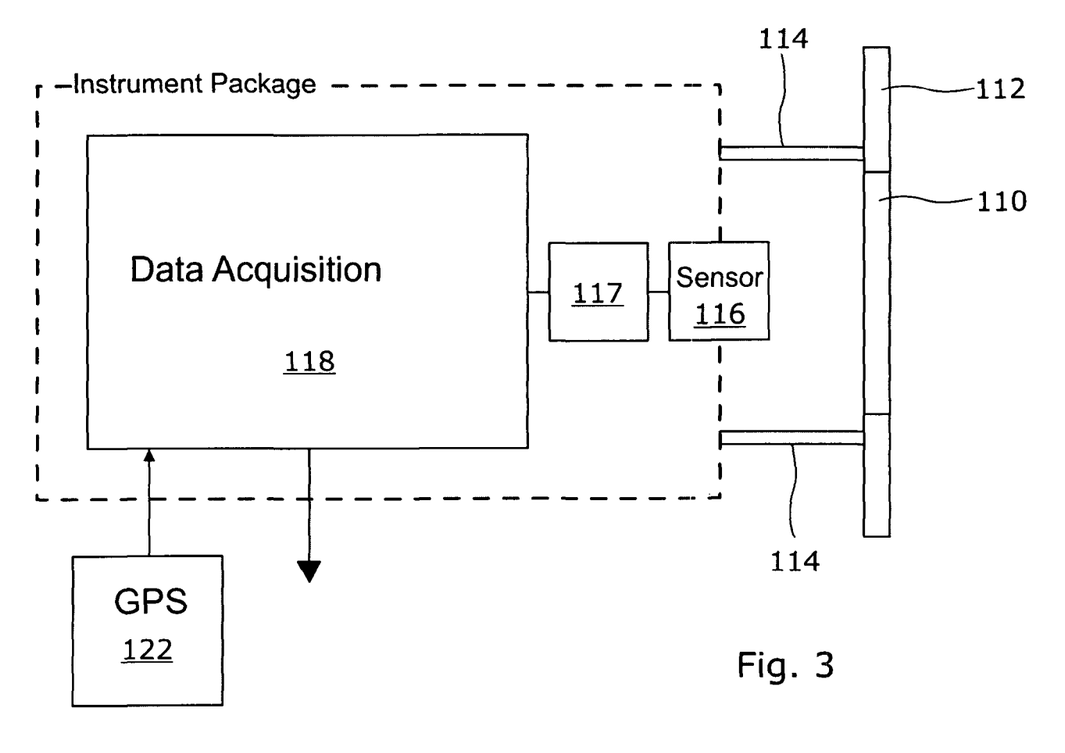
Figure 4:
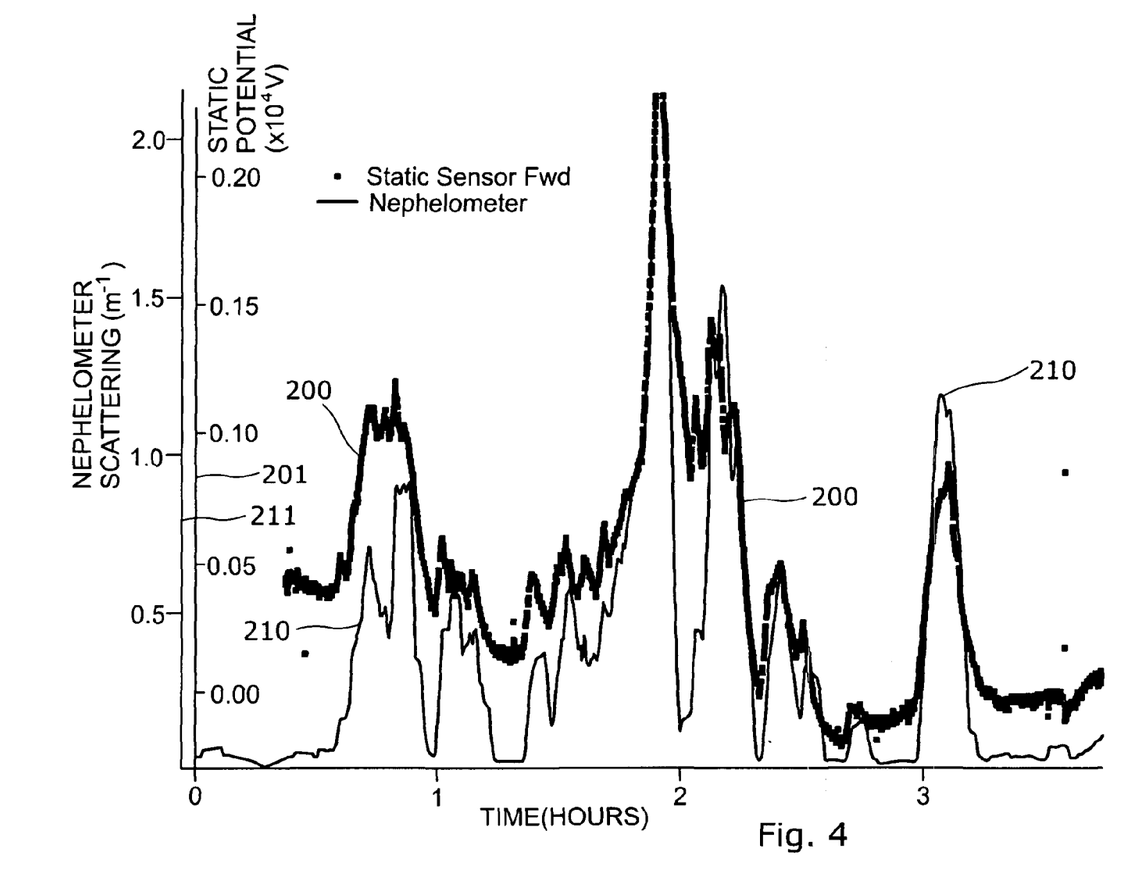

As an alternative to processing means arranged to convert values of the output of the static monitor, or the rate of change of output of the static monitor, stored in a data acquisition system to values of aerosol particle density, the apparatus may instead comprise processing means arranged to convert the output of the static monitor, or the rate of change of the output of the static monitor, directly (i.e. in real time) to a values of aerosol particle density on the basis of an assumed functional form for aerosol particle as a function of the output of the static monitor, or as the case may be the rate of change of the output of the static monitor. In this case the apparatus may further comprise a data acquisition system arranged to record values of aerosol particle density output by the processing means as a function of the position of the aircraft, so that the data acquisition system stores a mapping of aerosol particle density. In this case also, preferably the apparatus further comprises a global positioning system (GPS) arranged to output positional information for the aircraft to the data acquisition system for the reasons given above.

A second aspect of the invention provides a method of detecting particles in an aerosol comprising the step of causing an apparatus of the invention to pass through a region of the atmosphere containing the particles.

Embodiments of the invention are described below, by way of example only, and with reference to the accompanying drawings in which:

FIG. 1 shows a portion of a first example apparatus of the invention;

FIG. 2 shows a dielectric member of the FIG. 1 portion in more detail;

FIG. 3 shows a portion of a second example apparatus of the invention;

FIG. 4 shows traces of aerosol particle density obtained using a nephelometer and of the output of a static monitor comprised in apparatus of the invention;

FIG. 5 shows traces of aerosol particle density obtained using an optical spectrometer and of the output of a static monitor comprised in apparatus of the invention; and FIG. 6 shows traces of aerosol mass density obtained using dedicated instrumentation and of the rate of change of the output of a static monitor comprised in apparatus of the invention.

FIG. 1 shows a portion of a first example apparatus of the invention, the apparatus comprising a BAe '146' aircraft having metallic fuselage 12 having a window 10, an outer surface of which forms part of the exterior of the aircraft. An instrument package 20 is mounted on the interior of the aircraft, the instrument package 20 comprising an electro-mechanical field mill sensor 16 (e.g. model JCI 140 static monitor manufactured by Chilworth Technology Ltd, Southampton, U.K.). The output of the sensor 16 is coupled to a data acquisition system 18 which is arranged to record the output of the sensor 18 at regular intervals, each value of the output of the sensor 16 being recorded together with the position of the aircraft at the time the output is recorded. A global positioning system (GPS) unit 22 is arranged to supply positional information relating to the aircraft to the data acquisition system 18. A processor 24 coupled to the data acquisition system 18 is arranged to process information stored in the data acquisition system 18.

FIG. 2 shows the window 10 of the aircraft in more detail. The window 10 is made up of two structural layers 10A, 10B of acrylic, with a third internal layer 10C of acrylic which acts as a thin scratch panel. The outer surface of the layer 10A forms part of the exterior of the aircraft.

In use of the apparatus, the aircraft is flown through a region of the atmosphere containing particles of dust, ash, pollution etc, in other words a region of the atmosphere which is an aerosol. Aerosol particles which are charged and which impinge on the outer surface of the window 10 can transfer their charge to the outer surface of the window 10. In addition, uncharged particles which impinge on the window 10 can cause additional charging of the window 10 by a frictional mechanism. Charged and uncharged particles can also give rise to charging of parts of the exterior of the aircraft other than the outer surface of the window 10. As the aircraft is flown through the aerosol, the window 10 becomes polarised as a result of an electric field generated by one or more of these mechanisms. This polarisation gives rise to an induced charge on the interior of the window 10, and the electric field resulting from this induced charge is detected by the sensor 16. At each of a series of times, the output of the sensor 16 is recorded by the data acquisition system 18 together with the position of the aircraft as determined by the GPS 22.

The processor 24 is arranged to process data stored in the data acquisition system 18. The processor 24 may be carried on the aircraft and arranged to process the data in real-time or it may be used to process data off-line, with data only being stored whilst the aircraft is in flight. The processor 24 is arranged to convert recorded values of the output of the sensor 16 to values of particles density on the basis of an assumed functional relationship between the electric field due to induced charge on the interior of the window 10 (equivalent to the output of the static monitor 16) and particle density in the aerosol though which the aircraft is flown. In some situations the relationship may be very simple, e.g. the electric field (and hence the output of the sensor 16) may be directly proportional to aerosol particle density. In other cases the output of the sensor 16 may be a more complex function of particle density. In still further cases the rate of change of the output of the sensor 16 may be a linear or a more complex function of aerosol particle density. The functional relationship for a particular type of aerosol may be guessed or found previously from experience using other instruments or measurements. The processor 24 thus allows aerosol particle density as a function of position to be found, i.e. aerosol particle density to be mapped.

FIG. 3 shows a portion of a second example apparatus of the invention. Parts of the apparatus shown in FIG. 3 which correspond to parts of the apparatus shown in FIG. 1 are labelled with reference signs which differ by 100 from those labelling the corresponding parts in FIG. 1. In the second example apparatus the output of an electro-mechanical field mill sensor 116 is connected to a processor 117 which converts the output of the sensor 116 (or the rate of change of the output of sensor 116) in real-time to a value of aerosol particle density on the basis of an assumed functional form for aerosol particle density as a function of the output of the sensor 116 (or the rate of change of the output of the sensor 116). Output from the processor 117 corresponds directly to aerosol particle density, which is recorded at each of a series of times by a data acquisition system 118, together with the position of the aircraft as indicated by a GPS 122. The data acquisition system 118 therefore stores information mapping aerosol particle density as a function of position.

FIG. 4 shows a trace 210 of the output of an integrating nephelometer mounted on a research aircraft taken over a four hour period during which the aircraft was flown through a portion of the volcanic ash cloud produced by the eruption of the Eyjafjallajökull volcano in Iceland which began on 20 Mar. 2010. The trace 200 is referred to the vertical axis 211. The integrating nephelometer measures optical extinction over three visible wavelengths and its output is representative of aerosol particle density. FIG. 4 also shows a trace 200

(referred to vertical axis 201) of the output of an electro-mechanical field mill sensor over the same time period, the sensor being mounted within the same research aircraft in the manner indicated in FIGS. 1 and 3. FIG. 4 shows that the output of the electro-mechanical field mill was closely related to aerosol particle density as indicated by the extinction measured by the nephelometer.

Figure 5:
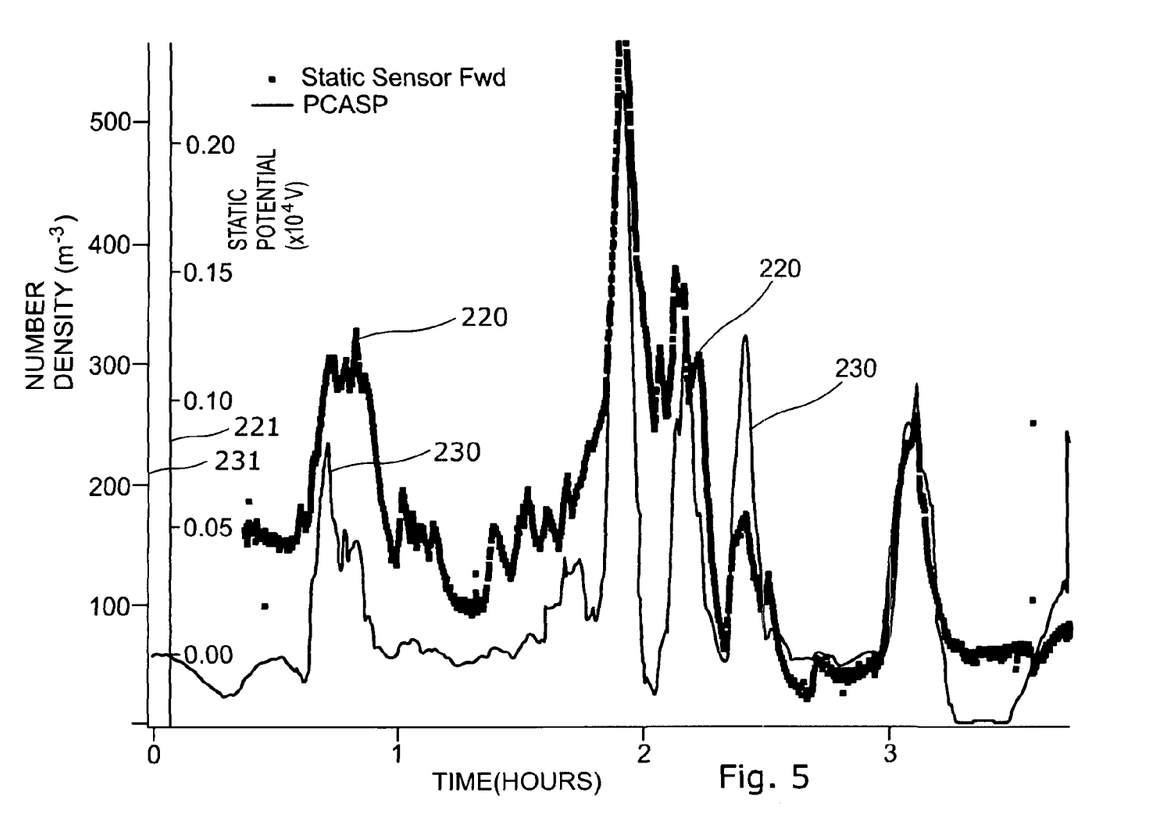

In FIG. 5, trace 220 (referred to vertical axis 221) is the same as trace 200 in FIG. 4. FIG. 5 also shows a trace 230 of the output of a passive cavity aerosol probe (PCASP), also mounted on the research aircraft, during the same four hour time period during which the trace 220 was recorded. (Trace 230 is referred to vertical axis 231). A PCASP is an optical spectrometer for detecting and analysing aerosols. FIG. 5 shows a close correlation between aerosol particle density, as measured by the PCASP, and the output of the electromechanical field mill sensor mounted within the research aircraft.

Figure 6:
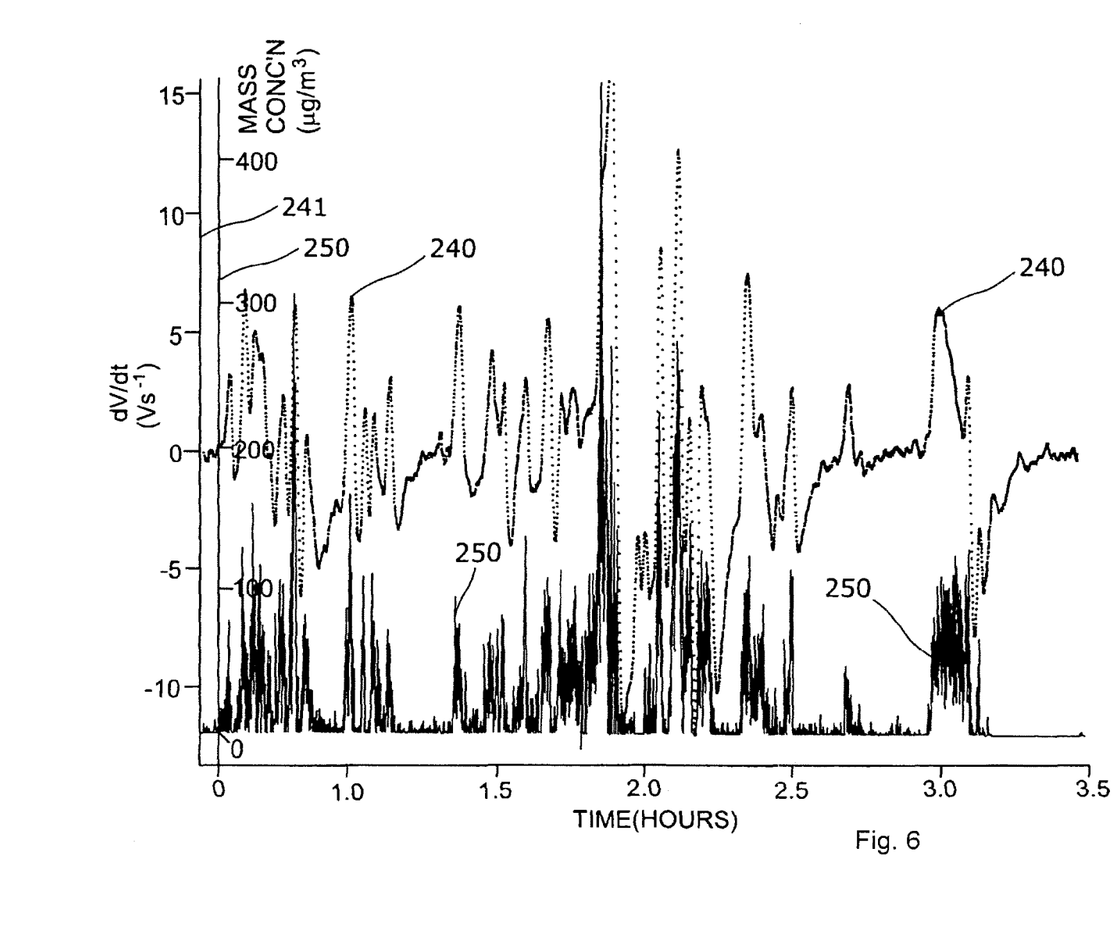

FIG. 6 shows a trace 240 of the rate of change of the output of the same electromechanical field mill sensor over a period of 3.5 hours (referred to vertical axis 241) and also a trace 250 of the mass concentration of volcanic ash over the same period as determined by a dedicated particle-density measuring instrument fixed to the research aircraft. FIG. 6 shows a close correlation between the rate of change of the output of the sensor and the aerosol particle density of the volcanic ash cloud through which the research aircraft was flown.

In some embodiments the output of the detection means may be monitored (e.g. input to a comparator) so that a warning signal may be generated if the output exceeds a threshold level associated with a level of aerosol particle density likely to damage the aircraft in some way (e.g. engine damage). The warning signal could be used to give a visual and/or audible signal to the pilot of the aircraft. Alternatively, or additionally, the warning signal may be used to automatically control the flight control systems of the aircraft so that the aircraft is steered to a region of airspace with a lower aerosol particle density.

The invention claimed is:

1. Aerosol detection apparatus comprising an aircraft having a dielectric member comprised in a body thereof such that a surface of the dielectric member forms part of the exterior surface of the aircraft, and a sensor located in the interior of the aircraft and arranged to detect an electric field within the aircraft, the electric field resulting from the dielectric member becoming polarised so that induced charge appears on a surface of the dielectric member opposite to that forming part of the exterior surface of the aircraft.

2. Apparatus according to claim 1 wherein the dielectric member comprises a window of the aircraft.

3. Apparatus according to claim 1, wherein the sensor comprises a static monitor mounted within the aircraft.

4. Apparatus according to claim 3 wherein the static monitor comprises an electro-static voltmeter.

5. Apparatus according to claim 4 wherein the electro-static voltmeter comprises an electro-mechanical field mill instrument.

6. Apparatus according to claim 3, further comprising an alarm configured to generate a signal if a monitored output of the static monitor exceeds a pre-determined threshold.

7. Apparatus according to claim 6, wherein the signal comprises at least one of:
 a visual signal for the attention of one of more members of the aircrew,
 an audible signal for the attention of the one or more members of the aircrew, and
 a control signal to the aircraft control systems, causing the aircraft to move out of a certain region of airspace.

8. Apparatus according to claim 3, further comprising a data acquisition system arranged to record one of the output of the static monitor and the rate of change of the output of the static monitor, as a function of the position of the aircraft.

9. Apparatus according to claim 8 wherein the apparatus further comprises a global positioning system arranged to output positional information for the aircraft to the data acquisition system.

10. Apparatus according to claim 8, further comprising a processor configured to convert one of recorded values of the output of the static monitor, and recorded values of the rate of change of the output of the static monitor, to values of aerosol particle density on the basis of an assumed functional form for aerosol particle density as a function of one of the output of the static monitor and the rate of change of the output of the static monitor.

11. Apparatus according to claim 3, further comprising a processor arranged to convert one of the output of the static monitor and the rate of change of the output of the static monitor to values of aerosol particle density on the basis of an assumed functional form for aerosol particle density as a function of one of the output of the static monitor and the rate of change of the output of the static monitor.

12. Apparatus according to claim 11 further comprising a data acquisition system arranged to record values of aerosol particle density output by the processor as a function of the position of the aircraft.

13. Apparatus according to claim 12 further comprising a global positioning system arranged to output positional information for the aircraft to the data acquisition system.

14. A method of detecting particles in an aerosol comprising of causing the apparatus according to claim 1 to pass through a region of the atmosphere containing the particles.

15. A method according to claim 14, wherein the region of the atmosphere contains dust or ash particles.

\* \* \* \* \*